United States Patent [19]
Huebner

[11] Patent Number: 5,658,283
[45] Date of Patent: Aug. 19, 1997

[54] EXTERNAL FIXATOR FOR REPAIRING FRACTURES

[76] Inventor: Randall J. Huebner, 18650 SW. Hart Rd., Aloha, Oreg. 97007

[21] Appl. No.: 715,017

[22] Filed: Sep. 17, 1996

Related U.S. Application Data

[63] Continuation-in-part of Ser. No. 636,326, Apr. 22, 1996, which is a continuation-in-part of Ser. No. 389,056, Feb. 15, 1995, Pat. No. 5,545,162.

[51] Int. Cl.$^6$ ............................................. A61B 17/60
[52] U.S. Cl. ............................ 606/57; 606/54; 606/62
[58] Field of Search ................................ 606/54, 55, 57, 606/59, 105, 62, 67

[56] References Cited

U.S. PATENT DOCUMENTS

| | | |
|---|---|---|
| 583,455 | 6/1897 | Bush . |
| 1,201,864 | 10/1916 | Overmeyer . |
| 1,789,060 | 1/1931 | Weisenbach . |
| 2,214,490 | 9/1940 | Thomas . |
| 2,250,417 | 7/1941 | Ettinger . |
| 2,251,209 | 7/1941 | Stader . |
| 2,333,033 | 10/1943 | Mraz . |
| 2,371,519 | 3/1945 | Haynes . |
| 2,391,537 | 12/1945 | Anderson . |
| 2,391,693 | 12/1945 | Ettinger . |
| 2,393,694 | 1/1946 | Kirschner . |
| 2,393,831 | 1/1946 | Stader . |
| 2,393,982 | 2/1946 | Giesen . |
| 2,406,987 | 9/1946 | Anderson . |
| 2,434,431 | 1/1948 | Pincock . |
| 2,435,850 | 2/1948 | Siebrandt . |
| 2,443,106 | 6/1948 | Grosso . |
| 2,697,433 | 12/1954 | Zehnder . |
| 2,812,761 | 11/1957 | Palkovitz . |
| 3,128,768 | 4/1964 | Geistauts . |
| 3,244,170 | 4/1966 | McElvenny . |
| 3,709,218 | 1/1973 | Halloran . |
| 3,835,849 | 9/1974 | McGuire . |
| 3,862,631 | 1/1975 | Austin . |
| 3,961,854 | 6/1976 | Jaquet . |
| 3,975,032 | 8/1976 | Bent et al. . |
| 4,003,096 | 1/1977 | Frey . |
| 4,040,130 | 8/1977 | Laure . |
| 4,096,857 | 6/1978 | Cramer et al. . |
| 4,127,119 | 11/1978 | Kronner . |
| 4,135,505 | 1/1979 | Day . |
| 4,220,146 | 9/1980 | Cloutier . |
| 4,244,360 | 1/1981 | Dohogne . |
| 4,271,832 | 6/1981 | Evans et al. . |
| 4,299,212 | 11/1981 | Goudfrooy . |
| 4,308,863 | 1/1982 | Fischer . |
| 4,338,927 | 7/1982 | Volkov et al. . |
| 4,349,017 | 9/1982 | Sayegh . |
| 4,393,868 | 7/1983 | Teague . |
| 4,409,970 | 10/1983 | Carrel . |

(List continued on next page.)

FOREIGN PATENT DOCUMENTS

| | | |
|---|---|---|
| 24 37 752 | 2/1976 | Germany . |
| 27 45 504 | 4/1979 | Germany . |
| 36 14 305 | 4/1986 | Germany . |
| 2 086 231 | 5/1982 | United Kingdom . |

OTHER PUBLICATIONS

"Distal Radius Fractures," by John M. Agee, MD. *External Fixation*, vol. 9, No. 4, Nov. 1993, pp. 577–585.

*Primary Examiner*—Michael Buiz
*Assistant Examiner*—Daphna Shai
*Attorney, Agent, or Firm*—Kolisch, Hartwell, Dickinson, McCormack & Heuser

[57] ABSTRACT

A fixation device for repairing a fracture of a bone having a medullary canal, where the device includes a radial transcutaneous pin configured to be mounted generally radially to the bone on a first side of the fracture and the radial transcutaneous pin includes an external free end. The device further includes an axial transcutaneous pin configured to enter the bone on a second side of the fracture and extend axially down the medullary canal with the axial transcutaneous pin including an external free end. An external member is configured to extend between the free ends of the pins and secure them relative to each other.

16 Claims, 8 Drawing Sheets

U.S. PATENT DOCUMENTS

| | | |
|---|---|---|
| 4,475,546 | 10/1984 | Patton . |
| 4,488,542 | 12/1984 | Helland . |
| 4,548,199 | 10/1985 | Agee . |
| 4,611,586 | 9/1986 | Agee et al. . |
| 4,628,919 | 12/1986 | Clyburn . |
| 4,913,137 | 4/1990 | Azer et al. . |
| 4,922,896 | 5/1990 | Agee et al. ................................ 606/57 |
| 4,988,349 | 1/1991 | Pennig . |
| 5,254,078 | 10/1993 | Carter et al. . |
| 5,281,224 | 1/1994 | Faccioli et al. . |
| 5,304,177 | 4/1994 | Pennig . |
| 5,320,622 | 6/1994 | Faccioli et al. . |
| 5,320,623 | 6/1994 | Pennig . |
| 5,352,228 | 10/1994 | Kummer et al. . |
| 5,571,103 | 11/1996 | Bailey ........................................ 606/62 |

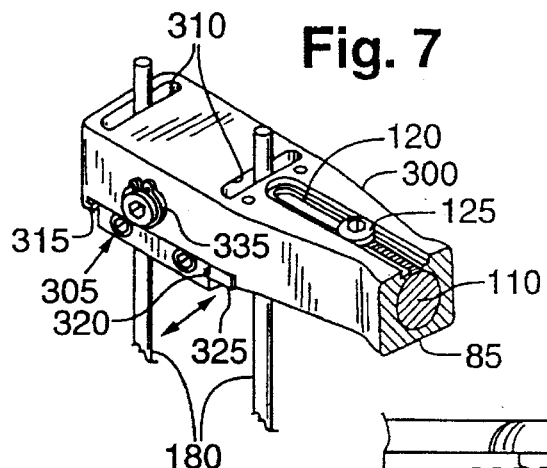
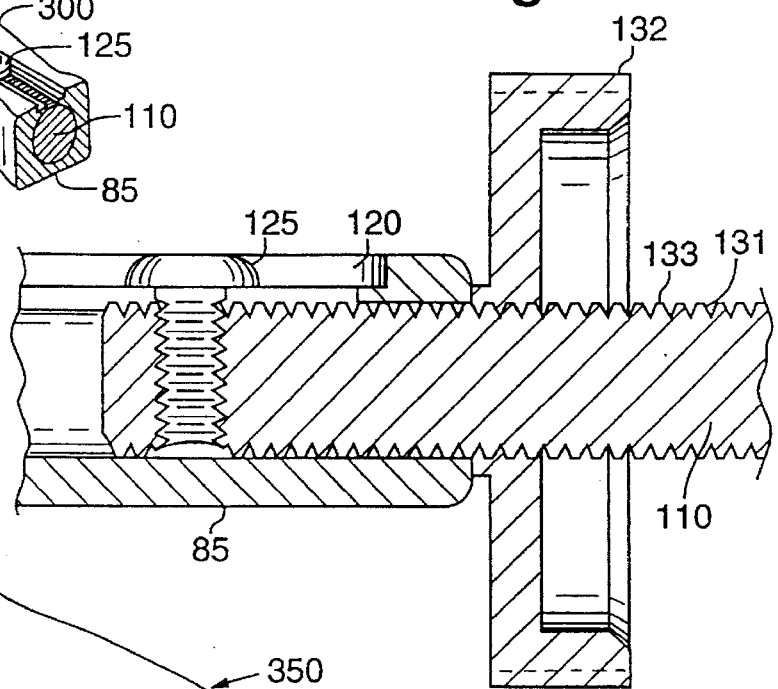
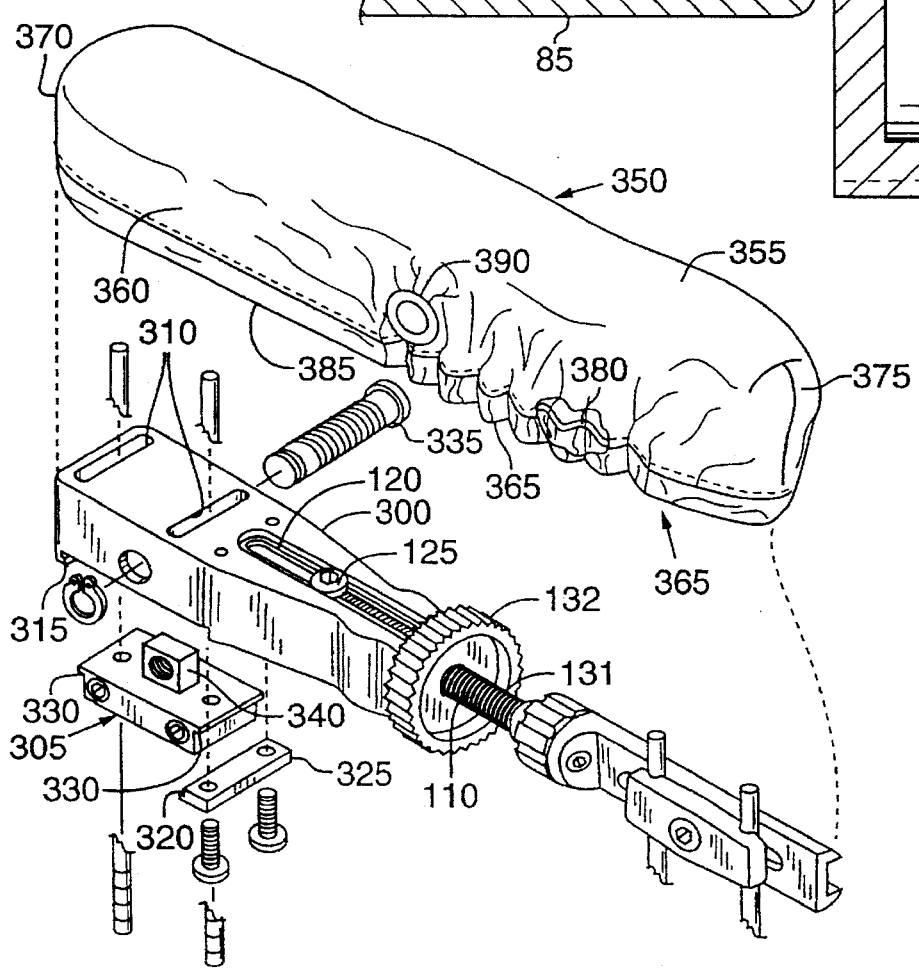

EXTERNAL FIXATOR FOR REPAIRING FRACTURES

CROSS REFERENCE TO RELATED APPLICATION

This application is a continuation-in-part of U.S. patent application Ser. No. 8/636,326 filed Apr. 22, 1996, still pending which is a continuation-in-part of U.S. patent application Ser. No. 08/389,056 filed Feb. 15, 1995, Now U.S. Pat. No. 5,545,1625.

FIELD OF THE INVENTION

This invention relates generally to a bone fixator for repairing fractures of the distal radius and wrist. More particularly, the invention is adapted to reduce and stabilize the relative positions of the fractured bone at the fracture site to promote proper healing and recovery.

BACKGROUND

The first external fixator was developed in 1843 for reducing and maintaining patellar fractures. Since then a large number of different fixators have been invented for splinting various bone fractures. Virtually all of these fixators have some features in common. In particular, they rely on transcutaneous pins or screws secured in the bone on either side of the fracture site. An external mechanism is attached to the pins and allows their relative positions to be adjusted. This enables the surgeon to reestablish alignment of the bone pieces at the fracture site. Once the bone is properly set, the articulations in the fixator are locked in place to maintain the chosen alignment.

The principal variations among the many fixator designs are the number of degrees of freedom provided and the relative independence of each articulation, both mechanical and geometric. The first fixator, for instance, was adjustable only in length and squeezed the fracture together by gripping opposed ends of the patella. Fixators designed to repair central fractures of the long bones typically have relatively few articulations or degrees of freedom. In contrast, fixators adapted to treat fractures of bones in the neighborhood of joints must provide many more degrees of freedom. Where there is not room to place the pins in the fractured bone between the fracture and the joint, the additional degrees of freedom are necessary because alignment must be established using pins placed in a bone on the far side of the joint from the fracture. For treatment of fractures near joints such as the wrist, which can rotate, flex and abduct, the fixator should offer some equivalent adjustment to accommodate the flexibility of the skeletal joint to allow the surgeon to establish the proper fracture alignment using forces transmitted through the joint.

Modern fixators tend to provide a large number of articulations of varying kinds. Probably the most common articulation is the ball joint. A ball joint provides one rotational and two pivotal degrees of freedom. A single setscrew or other locking mechanism can fix all three degrees of freedom simultaneously. The disadvantage of this type of articulation is that it is not possible to loosen the joint for motion in only one of the degrees of freedom without loosening it to move in other degrees of freedom. Thus, a surgeon cannot loosen the ball joint slightly to pivot it a small amount in one direction without the possibility of introducing changes affecting the other pivot and rotation settings.

In order to overcome this limitation, some fixators eliminate ball joints and rely instead on a combination of independent articulations to provide the necessary flexibility. The benefit of such a system is that each degree of freedom is mechanically independent of every other degree of freedom. A surgeon can thereby adjust the position of a single articulation in the fixator without affecting the settings of other articulations. Unfortunately, a given geometric readjustment of the bone ends at the fracture site may not correspond to an adjustment of any single articulation. Proper readjustment may require the surgeon to adjust several separate articulations, eliminating much of the benefit of independent articulations. Moreover, movement of one articulation may change some alignment of the bone ends previously established by another articulation.

With single degree of freedom articulations, such as simple pivots or slides, there are two basic adjustment techniques: gear-driven and free. Free articulations are typically freely adjustable until some type of lock is applied to secure the articulation at a selected setting. When the lock is loosened, the articulation is relatively free to move as the surgeon applies force to the joined members. Gear-driven articulations, in contrast, move under the control of some adjustment mechanism which provides mechanical advantage, such as a worm gear and rack or similar structure. Turning the worm gear causes the articulation to move incrementally in accordance with the rotation of the worm gear. This latter type of articulation generally provides the surgeon greater precision and control when making line adjustments, but hinders rapid gross corrections. It is possible to provide an articulation having both properties; however, in order to allow free motion of the articulation, the mechanical advantage provided by the gear reduction must be rather minimal. This would reduce the precision of the adjustment and negate the very purpose for which a gear drive would be used in the first place.

Most fixators also include some type of extensible/contractible articulation to permit the longitudinal spacing between the pins on opposite sides of the fracture to be controlled. This type of translational freedom can be used to accommodate individuals of varying size, as well as to distract the fracture, if necessary. In addition, for general purpose fixators which are not designed for a specific fracture, translational degrees of freedom can be used to create whatever spacing is required on either side of the fracture to allow for proper pin placement.

Fixators may be either general purpose or fracture specific. General purpose fixators are designed with considerable flexibility to accommodate many different types of fractures whereas fixators intended for use on a specific type of fracture typically have fewer degrees of freedom. In addition, the articulations provided are usually tailored to correct for specific fracture displacements. Likewise, for fractures too close to a joint to permit pin placement on both sides of the fracture, the articulations are adapted to compensate for varying joint position. Articulations corresponding to joint movements may also be used to set the joint in a comfortable position, as well as align the ends of the bone at the fracture site.

One of the more common fractures requiring a fixator for proper treatment is a fracture of the distal radius, or Colles fracture. This type of fracture usually results from a fall on an outstretched hand. The fracture line is usually quite close to the distal head of the radius and sometimes the head is comminuted. Because of the lack of space and the number of tendons and nerves in the area, it is difficult to mount pins in the radius on the distal side of the fracture. Therefore, such fractures are typically reduced using a pair of pins set in the metacarpal bone and a pair of pins set in the radius on the proximal side of the fracture. In order to avoid damage to tendons and nerves, the radial pins are usually set in the third quarter of the radius, i.e., the proximal half of the distal half of the radius. With the pins are set on opposite sides of the wrist joint; the fixator must be sufficiently articulated to reduce the fracture using forces transmitted through the wrist joint.

The wrist joint permits the hand to move in three-degrees of freedom relative to the forearm. First, the hand can move in supination and pronation, i.e., the rotation about the longitudinal axis of the forearm. Second, the hand can move in abduction and abduction, i.e., pivoting about an axis perpendicular to the plane of the palm. The last type of mobility of the hand is flexion and extension, which is the pivotal motion about an axis in the plane of the palm and perpendicular to the longitudinal axis of the forearm.

Because of the difficulty of accommodating the flexibility of the wrist joint, it would be beneficial to apply fixation directly to the severed agent of the radius. This would have the substantial benefit of allowing the continued use of the hand and wrist by the patient. Allowing mobility in the wrist joint prevents a number of possibly serious complications, such as a permanent loss of range of motion. Unfortunately, the tendons and nerves running over the distal end of the radius make use of a standard pin difficult.

It is known to use one or more transcutaneous intermedullary wires that enter the radius at the distal end and extend part way down the medullary canal. Such wires operate essentially like a nail, i.e., they prevent the fractured pieces from moving laterally and offer some frictional resistance to longitudinal displacement. This form of wire fixation however, does not allow the fragment to be manipulated as can be accomplished with articulated external fixators.

In addition to the requisite physical characteristics of a fixator, it is important to consider the psychological impact of the fixator on the patient. The sight of pins passing through the wearer's skin can be distressing to the wearer, as well as other people who may come into contact with the wearer. This may be particularly true during meals and in public. It is therefore desirable to mitigate the deleterious psychological impact of wearing a fixator, to whatever extent possible.

It is therefore an object of the present invention to provide a fixator for use on fractures of the distal radius or wrist It is another object of the present invention to provide a fixator for use on fractures of the distal radius that is articulated to allow adjustment of each of the three-degrees of freedom of the wrist.

It is an additional object of the present invention to provide a fixator, for use on fractures of the distal radius, that provides a sufficient range of mobility to accommodate wrist flexibility and imprecise pin placement and still have enough travel left to reduce the fracture.

It is yet another object of the present invention to provide a fixator for use on fractures of the distal radius with enough free articulations to facilitate easy mounting on the support pins after they are installed in the radius and metacarpal bones.

An additional object of the present invention is to provide a fixator for use on fractures of the distal radius that allows the surgeon to achieve accurate and rapid reduction of the fracture.

One more object of the present invention is to provide a fixator including an enveloping cover to make the fixator more cosmetically acceptable.

Another object of the present invention is to provide a fixator that can be coupled directly to the distal fragment on a distal radius fracture.

An additional object of the present invention is to provide an external fixator that includes an intermedullary portion to enhance fracture stability.

These and other objects and advantages will be more clearly understood from a consideration of the accompanying drawings and the following description of the preferred embodiment.

SUMMARY OF THE INVENTION

The present invention is a bone fixator for repairing fractures of the distal radius and wrist. It includes, in the preferred embodiment, at least two generally parallel spaced-apart elongate distal mounting pins with lower ends for mounting in the metacarpal bone and at least two generally parallel spaced-apart elongate radial mounting pins with lower ends for mounting in the radius. A distal pin clamp assembly secures the distal pins to an elongate distal member. The clamp assembly and pins are movably coupled to the distal member for translational movement along its elongate axis and pivotal motion about a pivot axis generally perpendicular to the elongate axis of the distal member and the elongate axes of the distal pins. The fixator further includes a proximal pin mounting block for securing the radial pins and an elongate medial assembly of adjustable length. The medial assembly is pivotally connected at one end to the pin mounting block for independent pivotal motion about an axis generally parallel to the elongate axes of the proximal mounting pins and coupled at the opposed end through a ball joint to the distal member.

In an alternative embodiment, a pin carriage block holds the radial pins and is coupled to the medial assembly for independent translational motion perpendicular to the axis of the pins and the longitudinal axis of the radius. In addition or alternatively, the medial assembly may include a mechanically driven extension/distraction mechanism.

In another embodiment the invention is a fixation device for repairing a fracture of a bone having a medullary canal, where the device includes a radial transcutaneous pin configured to be mounted generally radially to the bone on a first side of the fracture and the radial transcutaneous pin includes an external free end. The device further includes an axial transcutaneous pin configured to enter the bone on a second side of the fracture and extend axially down the medullary canal with the axial transcutaneous pin including an external free end. An external member is configured to extend between the free ends of the pins and secure them relative to each other.

BRIEF DESCRIPTION OF THE DRAWINGS

FIG. 7 is a perspective view of the proximal end of an alternative embodiment of a fixator according to the present invention.

FIG. 8 is a perspective, partially exploded view of the fixator of FIG. 7.

FIG. 9 is a partial cross-sectional view of a portion of the fixator of FIGS. 7 and 8.

DETAILED DESCRIPTION OF THE PREFERRED EMBODIMENT

Figure 1:
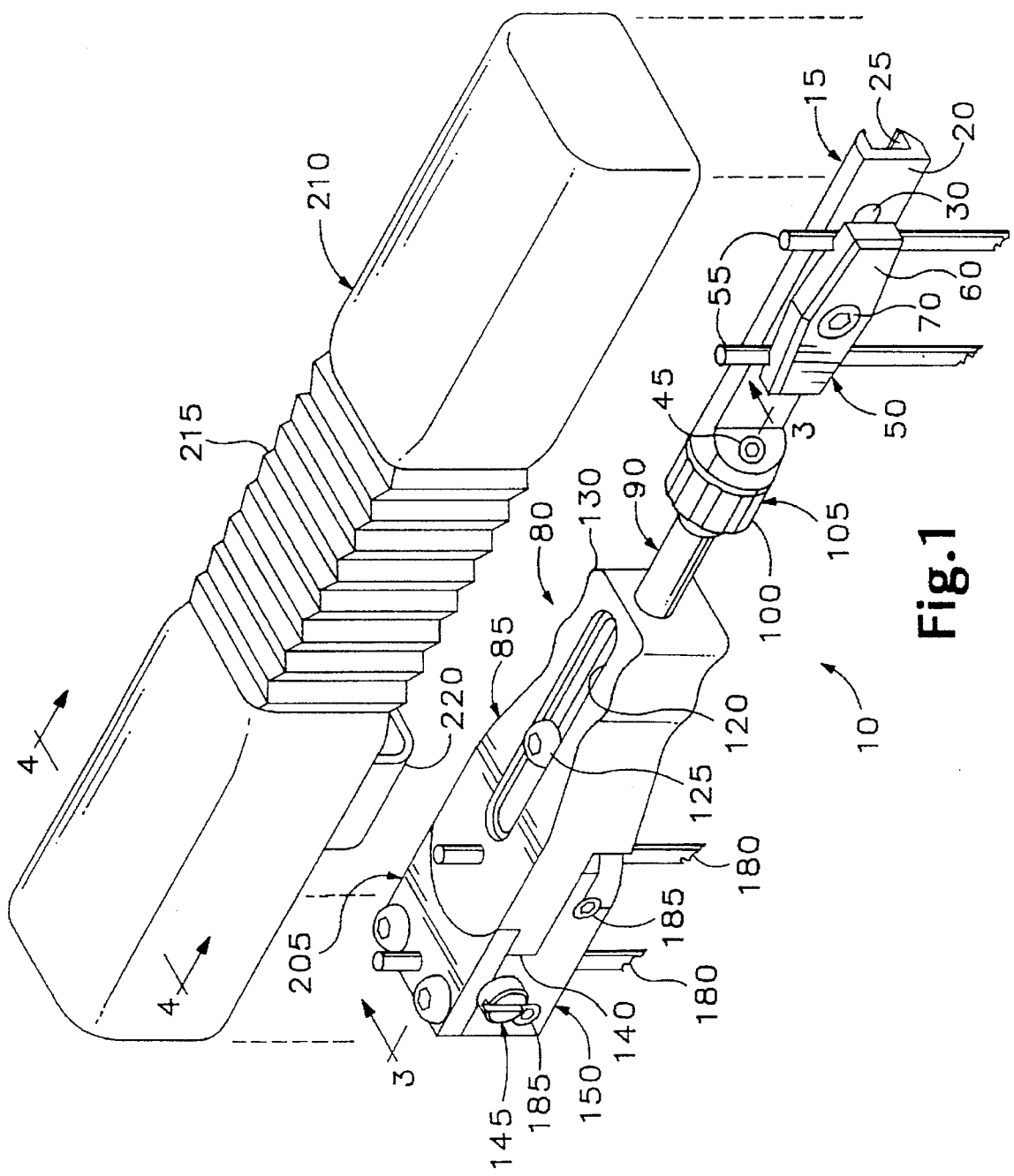
FIG. 1. is a perspective view of a fixator and cover according to the present invention.
Figure 2:
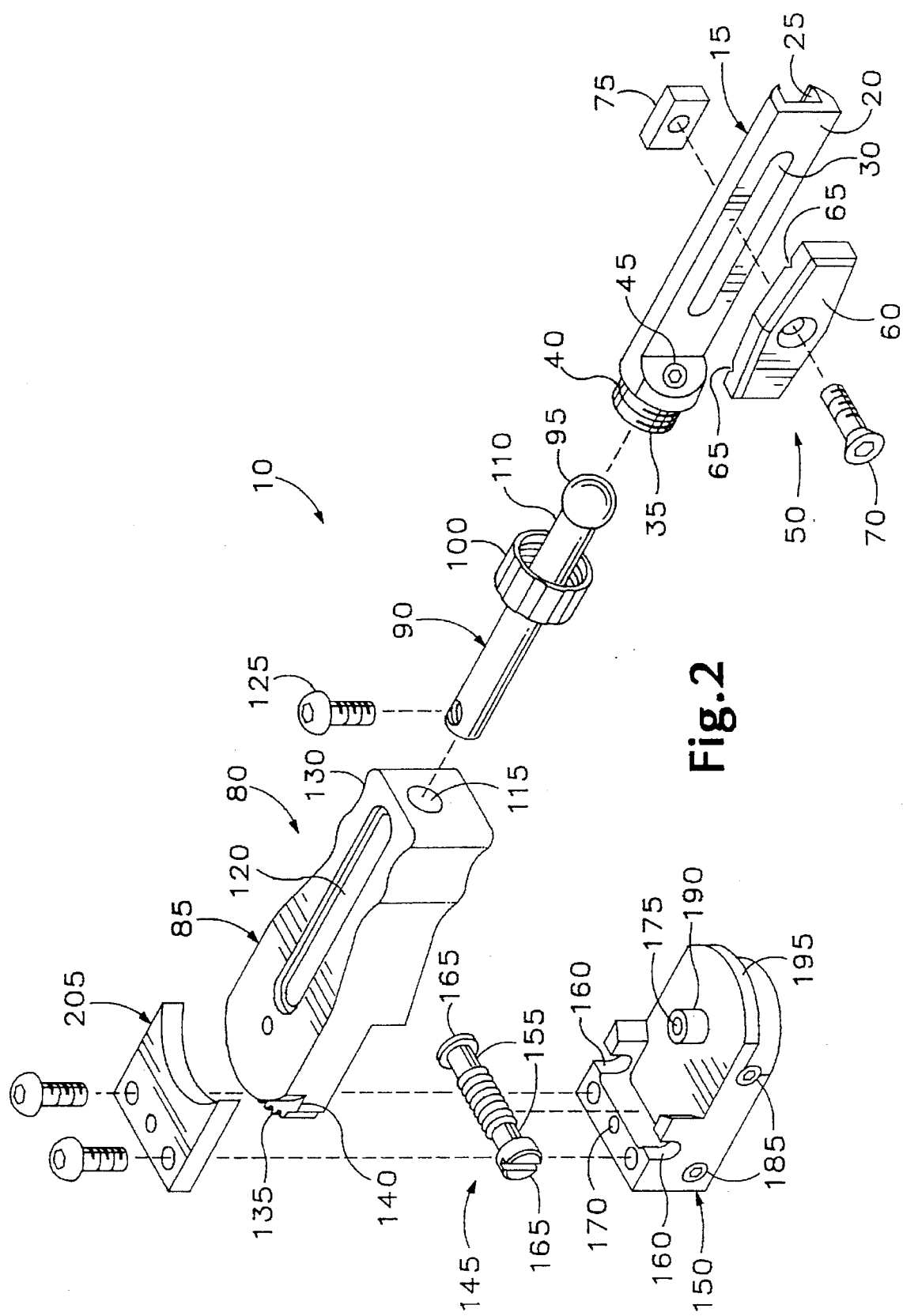
FIG. 2 is an exploded perspective view of the fixator of FIG. 1.
Figure 3:
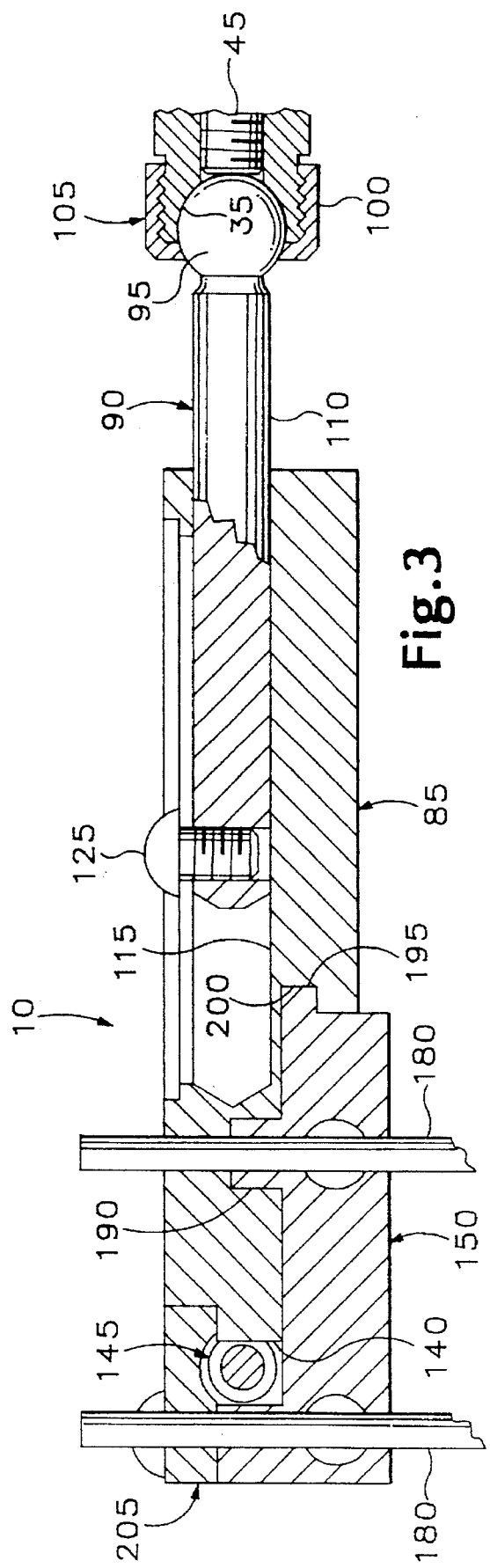
FIG. 3 is a cross-sectional view along line 3—3 in FIG. 1.

A fixator according to the present invention is shown generally at 10 in FIGS. 1 and 2. An elongate distal member 15 forms the distal end of fixator 10. A generally planar pin shelf 20 and opposed nut track 25 extend along the length of distal member 15. An elongate slot 30 extends along distal member 15, forming a passage between track 25 and shelf 20. At the proximal terminus of distal member 15 is a semi-spheroidal cup 35 with externally threaded walls 40. See FIG. 3. A setscrew 45 extends through a portion of distal member 15 into the bottom of cup 35. The axis of setscrew 45 is aligned to intersect with the center of the sphere defined by cup 35.

A pin clamp assembly 50 secures two distal pins 55 to distal member 15. Pin clamp assembly 50 includes a clamp plate 60 with a transverse groove 65 formed at either end to receive distal pins 55. Clamp plate 60 is urged against shelf 20 by a clamp screw 70 which extends through slot 30 and into nut track 25. Clamp screw 70 is engaged in a pin clamp nut 75 which rides in nut track 25. When clamp screw 70 is tightened, clamp nut 75 is urged against the bottom of nut track 25 and clamp plate 60 is urged against shelf 20 thereby trapping pins 55 between clamp plate 60 and shelf 20.

When clamp screw 70 is loosened, pin clamp assembly 50 is free to travel back and forth along the length of distal member 15, limited only by the extent of nut track 25 and slot 30. Clamp plate 60 can additionally pivot about clamp screw 70. These motions allow pins 55 to be positioned as desired along distal member 15, as well as pivoted in the plane of shelf 20 about the axis of clamp screw 70.

An elongate medial assembly 80, including an elongate medial block 85 and a ball rod 90 is coupled to distal member 15 by a ball 95 at the distal end of ball rod 90. Ball 95 fits in cup 35 and is retained therein by a ball joint cap 100 to form a ball joint 105. Ball joint cap 100 is internally threaded and screws down over externally threaded walls 40. When cap 100 is fully seated over cup 35, ball joint 105 should still move relatively freely, allowing ball rod 90 to be positioned anywhere within a cone with an apex at the center of ball 95 and a side angle of approximately 20–30-degrees from the axis of distal member 15. Ball rod 90 can also be rotated about its axis without restriction in ball joint 105. Setscrew 45 fixes the orientation of ball joint 105 when tightened. If setscrew 45 is only lightly tightened, it will create some drag on the motion of ball joint 105, while still allowing some movement.

Ball 95 is mounted on a shaft 110, which is in turn telescopically engaged in a longitudinal bore 115 in medial block 85 to make media/assembly 80 adjustable in length. An elongate aperture 120 opens onto bore 115 from the upper surface of medial block 85. A setscrew 125 mounted in the proximal end of shaft 110 slides in aperture 120 and serves to lock ball rod 90 in place when desired. Setscrew 125 also prevents ball rod 90 from rotating in bore 115. A grip 130 is incorporated in medial block 85 generally over bore 115 to accommodate the surgeon's fingers.

In an alternative embodiment, shown in FIGS. 7 and 8, shaft 110 includes threads 131 formed along its outer surface. A knurled nut 132 fits over thread 131 between ball 95 and the distal end of medial block 85. When the nut is adjacent to the block, further rotation of the nut toward the block causes the ball rod to be extended from the bore. This gives the surgeon the ability to precisely control the distraction of the fracture. Another benefit of the embodiment shown in FIGS. 7 and 8 is that the nut can be quickly spun up to the ball, allowing the telescopic adjustment of the fixator to be freely adjusted for attachment to the pins, while retaining the precision of a mechanical adjustment during reduction of the fracture. It should be noted that, in the preferred embodiment, thread 131 has a flattened crest 133 to allow it to slide more freely in bore 115. See FIG. 9.

The proximal end of medial block 85 includes an arcuate rack 135 formed on the end of a protruding ledge 140. Arcuate rack 135 co-acts with a worm gear 145 to control the position of a proximal pin mounting block 150, which is pivotally connected to medial block 85. Worm gear 145 includes bearing surfaces 155 near each end that ride in a pair of U-shaped guides 160 formed in pin mounting block 150. A flared head 165 at each end prevents worm gear 145 from moving side-to-side in pin mounting block 150.

Proximal and distal transverse openings 170, 175 extend through pin mounting block 150 to receive a pair of radial pins 180. Each transverse opening 170, 175 includes an associated setscrew 185 to secure radial pins 180. A pivot guide 190 surrounds the upper potion of distal opening 175 and medial block 85 fits over and pivots around pivot guide 190. An arcuate lip 195 on the distal end of pin mounting block 150 is received in a matching pivot slot 200 in medial block 85. See FIG. 3. The interaction of lip 195 in pivot slot 200 helps to secure medial block 85 to pin mounting block 150. A retainer plate 205 is screwed to the proximal end of pin mounting block 150 and extends over ledge 140 to further secure medial block 85 to pin mounting block 150.

An alternative embodiment of the proximal end of the present invention is shown in FIGS. 7 and 8. In the fixator of FIGS. 7 and 8, a medial block 300 extends back to the proximal end of the fixator, thus eliminating pin mounting block 150. Medial block 300 includes a pair of transverse slots 310 through which radial mounting pins 180 extend. Slots 310 allow the pins to be shifted in the dorsal or palmar direction by approximately three-eighths of an inch from center. The pins are carded by a pin mounting carriage 305 which replaces pin mounting block 150.

It should be noted that one of the advantages of the design of medial block 300 is that it can be manufactured from radiolucent materials, preferably UltemJ. Use of radiolucent materials is beneficial because the surgeon can take X-rays from angles that would otherwise be obstructed by the medial block if it were not radiolucent.

Carriage 305 mounts to the lower surface of media/block 300 and rides on a pair of projecting ledges 315, 320. Ledge 315 is formed on block 300 and ledge 320 is formed on a retention plate 325 that is screwed to the bottom of the block. Carriage 305 includes a flange 330 at each end to engage the ledges. The carriage is conveyed dorsally and laterally by a lead screw 335 is rotatably mounted in block 300 and extends from the dorsal to the palmar side thereof. A pedestal 340 projects upwardly from the top of carriage 305 to engage lead screw 335. When the lead screw is rotate the pedestal and the carriage are conveyed either dorsally or palmarly on the screw, thus shifting position of the distal portions of the fixator relative to the radial pins. It should be noted that this is a pure palmar/dorsal translation with no pivotal component as occurs when medial block 85 is pivoted relative to pin mounting block 150.

Figure 4:
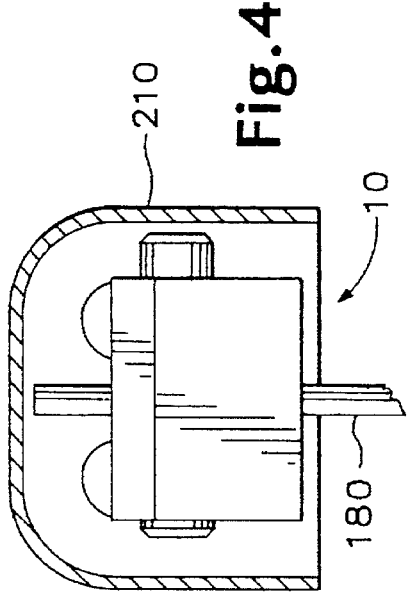
FIG. 4 is a cross-sectional view along line 4—4 in FIG. 1, showing how the cover fits over the fixator.

A cover 210 is provided to envelope and cloak fixator 10. See FIGS. 1 and 4. Cover 210 is preferably formed of thin flexible plastic. A bellows 215 in the middle of cover 210 allows the length to be adjusted to match the length of fixator 10 as installed on the patient. Although not shown, cover 210 could be formed as two telescoping pieces to achieve the same effect. A Velcro J strap 220 or other fastener may be use to secure cover 210 to fixator 10.

An alternative cover is shown at 350 in FIG. 7. Cover 350 includes a top 355 and downwardly depending sides 360 extending around the perimeter of the top to form a cavity 365 open on one side. The cover is preferably formed of two panels of a flexible fabric material separated by a thin layer of batting. The panels are folded downward and stitched together at proximal and distal ends 370, 375, respectively, to form sides 360 and cavity 365 to enclose the fixator. An elastic band 380 is stitched into a portion of a lower edge 385 of the cover to help the cover conform to the various configurations of the fixator. A closure mechanism in the form of snap 390 is provided to join the opposed lower edges of the cover to secure it in place on a fixator.

The first step in the process of installing fixator 10 on a patient is placing distal pins 55 in the patient's metacarpal and radial pins 180 in the radius. Pins 55, 180 are installed with the aid of a drill guide, not shown, which includes two spaced-apart parallel guide holes. The drill guide insures that the two pins in each bone are parallel to one another, and generally perpendicular to the longitudinal axis of the bone. In both locations the inter-pin spacing is about 25 mm in the preferred embodiment. The two pins in each pair should generally be as close together as possible to minimize the size of the incision required for placement and allow treatment of small patients, but they must also be far enough apart to provide adequate rigidity for reduction of the fracture.

Figure 5:
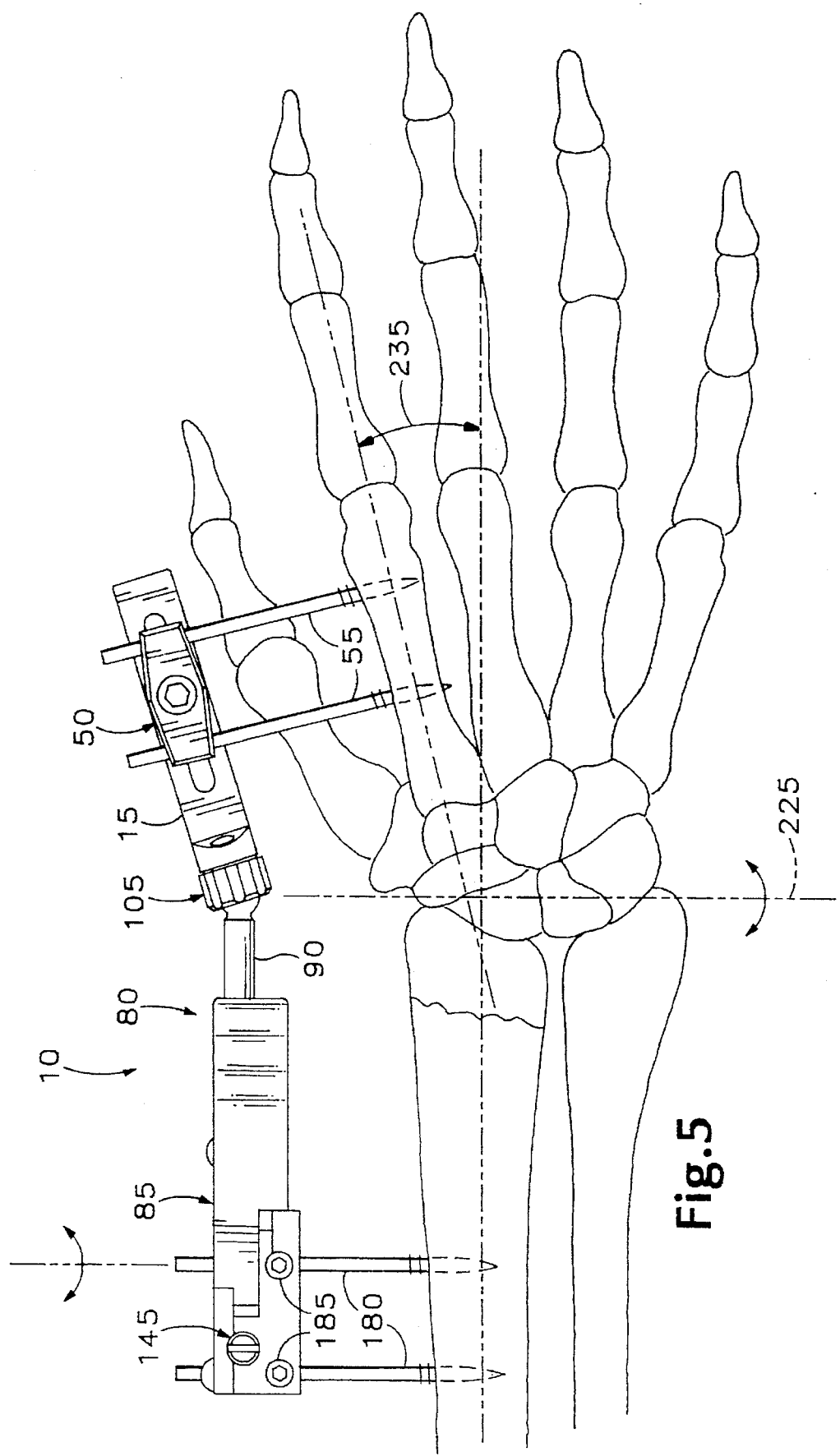
FIG. 5 is a side view of the fixator as it would be mounted on a patients arm.
Figure 6:
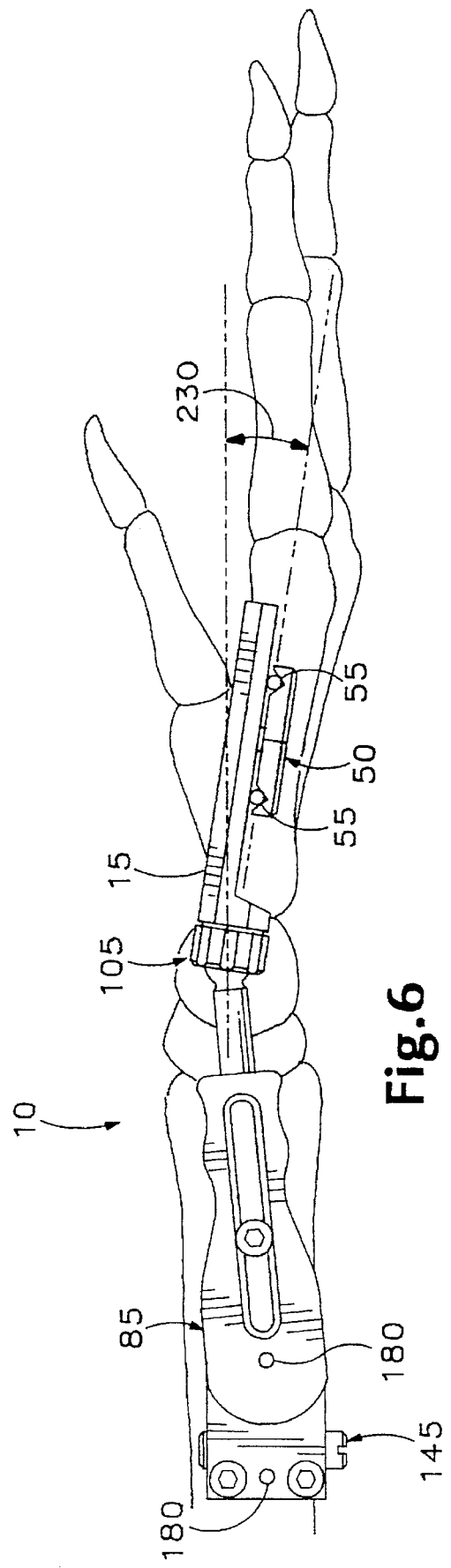
FIG. 6 is a top view of the fixator as it would be mounted on a patients arm.

After pins 55, 180 are properly installed, fixator 10 is attached. In order to place fixator 10 on pins 55, 180, it is desirable to loosen all of the free articulations so fixator 10 may be freely adjusted. With all the free articulations loosened, fixator 10 is quite limber, making the task of installing it on pins 55, 180 relatively quick and easy. Once fixator 10 is mounted on the pins, the relative positions of pin clamp assembly 50 along distal member 15 and ball rod 90 in medial block 85 are adjusted so that ball 95 is placed over the flexion/extension axis 225 of the wrist. See FIG. 5. Aligning the pivot axis of ball joint 105 with the flexion axis 225 of the wrist allows the patient's wrist to be set to the desired extension angle 230, typically 15-degrees, without disturbing the alignment of previous adjustments. See FIG. 6.

The travel of distal pins 55 along distal member 15 is used to accommodate variation in the spacing between the center of the wrist and the metacarpal, which depends on the size of the patient's hand. Media/assembly 80, similarly, telescopes to fit patients with longer or shorter forearms. Because the telescopic action of medial assembly 80 compensates for part of the variation of spacing between the distal and radial pins among individuals, the overall length of fixator 10 can reduced according to the size of the patient, making it less bulky and less likely to bump or snag on other objects around the patient than a fixator of fixed length.

The rotation of distal member 15, and therefore distal pins 55, allowed by ball joint 105 allows fixator 10 to accommodate distal and radial pins 55, 180 which are not parallel to each other. This flexibility makes alignment between distal pins 55 and radial pins 180 much less critical. The rotation also allows the supination and pronation of the patient's hand to be adjusted. As supination is adjusted, the pivot joint between media/block 85 and pin mounting block 150 must be changed to compensate for displacement of the fracture alignment since the axis of rotation of ball joint 105 is not coincident with the axis of rotation of the wrist.

The pivotal motion between distal pins 55 and distal member 15, in conjunction with displacement of distal pins 55 along distal member 15, allows the abduction angle 235 of the patient's wrist to be set to the desired value, which is typically 14-degrees. See FIG. 5. Likewise, the combined pivotal action of distal pins 55 on distal member 15 and distal member 15 on ball 95 can be used to set the radial/ulnar fracture alignment.

If distraction of the fracture is required, the length of medial assembly 80 is adjusted accordingly. This adjustment leaves ball 95 properly placed over flexion/extension axis 225 of the wrist. The dorsal/palmar alignment of the fracture site is adjusted using worm gear 145 to pivot medial assembly 80 relative to pin mounting block 150. In the alternative embodiment shown in FIGS. 7 and 8, the length of the medial assembly, and therefore distraction of the fracture, is adjusted using nut 132, which allows greater precision and control. Likewise, with the embodiment shown in FIGS. 7 and 8, the dorsal/palmar alignment is adjusted using the lead screw. This eliminates the angular movement inherent in pivoting medial assembly 80 relative to pin mounting block 150 to correct dorsal/palmar misalignment at the fracture site. As previously discussed, achieving proper reduction of fractures can be simplified if the various adjustments provided by the fixator are independent of one another.

With the exception of the pivot joint between pin mounting block 150/carriage 305 and medial block 85, each of the articulations in fixator 10 can be gradually tightened to provided increasing resistance to movement. This permits quick manual adjustment of the articulations, but otherwise holds them relatively fixed. Once the desired alignment of the fracture and wrist position are established, all of the articulations are locked in place.

Figure 10:
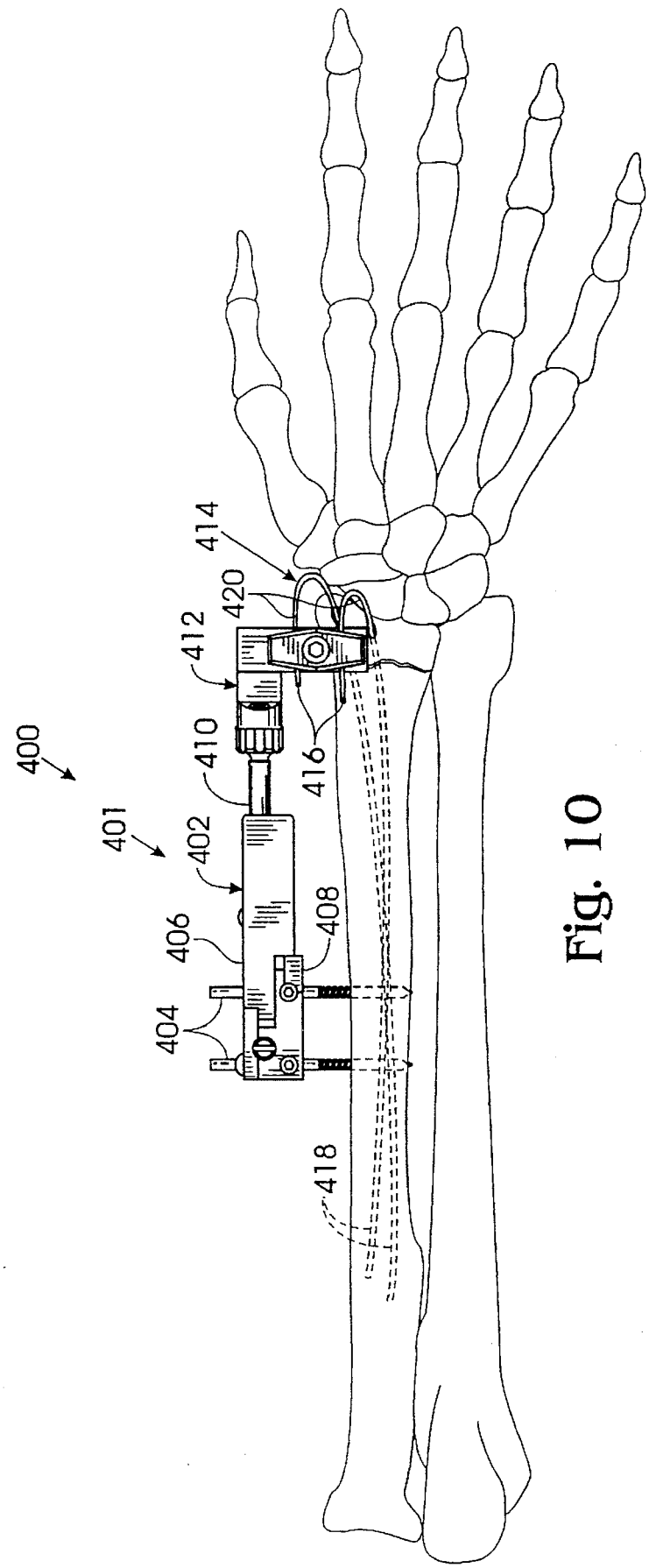
FIG. 10 is a side view of an alternative embodiment of a fixation device according to the present invention.

Another external fixator according to the present invention is shown generally at 400 in FIG. 10. Fixator 400 includes an external member 401 with a proximal portion 402, preferably constructed according to the structure shown in FIGS. 7 and 8, and configured to be mounted to the radius on a pair of radially oriented proximal transcutaneous mounting pins 404. Proximal portion 402 includes a medial block 406 and a pin mounting carriage 408 configured to secure pins 404 and coupled to the bottom of the block for transverse sliding motion relative thereto. A ball rod 410 is telescopically mounted in the distal end of block 406 and joined to a distal member 412.

Distal member 412 is generally similar to distal member 15 shown in FIG. 1, but projects transversely toward the arm above the distal end of the radius. This configuration allows distal member 412 to secure a pair of intermedullary pins 414. Distal member 412 clamps pins 414 at their free ends 416. As shown in FIG. 10, the pins have elongate axial or intermedullary portions 418 configured to be installed longitudinally down the medullary canal of the bone and transcutaneous sections 420 configured to extend through the skin and bone between the intermedullary portions 418 and the free ends 416. It should be noted that the pins preferably extend across the fracture and thereby provide enhanced lateral stability. Intermedullary portions 418 may also extend past pins 404.

Pins 414 typically are installed by flexing the wrist palmarly and pushing the end of the pin, which has been sharpened, through the distal tip of the radius. After installation, the fixator is clamped to the pins and reduction of the fracture is carded out essentially as described above for a fixator using metacarpal pins.

Figure 11:
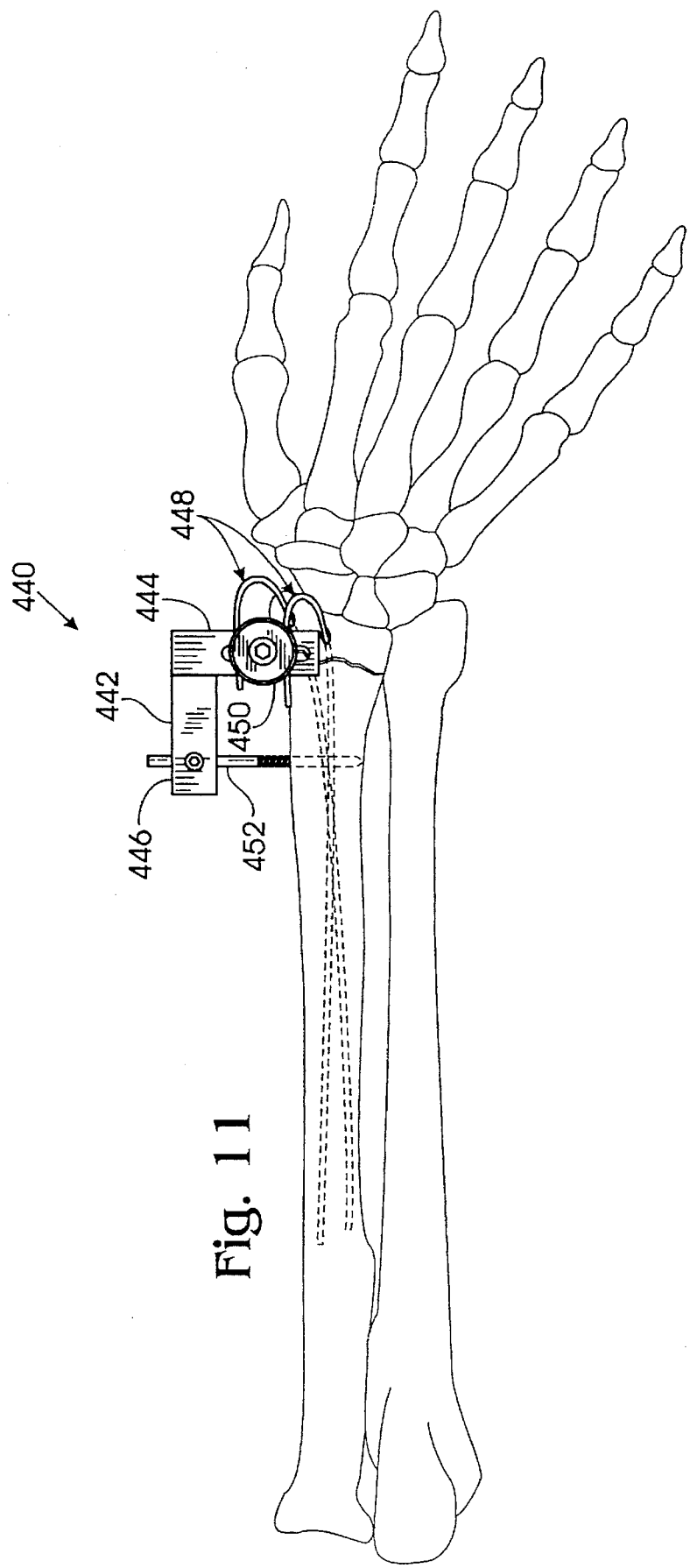
FIG. 11 is a side view of another alternative embodiment of a fixation device according to the present invention.

FIG. 11 illustrates a simplified version of the fixator of FIG. 10. In particular, FIG. 11 shows a fixator 440 consisting of a single L-shaped bracket 442, with a distal clamping section 444 and a proximal radial pin mounting portion 446. Distal clamping section 444 is constructed similarly to distal member 412 and is configured to capture a pair of intermedullary pins 448 with a pin clamp assembly 450. Pin clamp assembly 450 can slide up and down along clamping section 444 allowing the positioning of the pins to be adjusted. It should be noted that there are no articulations between the mounting portion and the clamping section. However, because pin clamp assembly 450 can rotate and slide along clamping section 444, it provides a considerable range of adjustment in positioning pins 448 and reducing the fracture. Mounting portion 446 of fixator 440 fits over a radial pin 452 and is held in place thereon by a set screw. Bracket 442 can slide up and down on radial pin 452 to provide additional adjustment during fracture reduction.

Although the fixators of FIGS. 10 and 11 are shown in the context of repairing fractures of the distal radius, the technique of using intermedullary pins in connection with an external member could be applied to treat other fractures as well. The same technique could also be applied for use with an intermedullary rod rather than pins. In this case the external portion would be joined to the intermedullary rod by pins extending through the bone and connecting to the rod. It should also be noted that the fixators of FIGS. 10 and 11 could be implemented using two sets of intermedullary pins rather than one intermedullary set and one radially oriented set.

It will now be clear that an improvement in this art has been provided which accomplishes the objectives heretofore set forth. While the invention has been disclosed in its preferred form, it is to be understood that the specific embodiment thereof as disclosed and illustrated herein is not to be considered in a limited sense as there may be other forms or modifications which should also be construed to come within the scope of the appended claims.

It Is claimed and desired to secure by Letters Patent:

1. A fixation device for repairing a fracture of a bone having a medullary canal, the device comprising:

a radial transcutaneous pin configured to be mounted generally radially to the bone on a first side of the fracture, the radial transcutaneous pin including an external free end;

an axial transcutaneous pin configured to enter the bone on a second side of the fracture and extend axially down the medullary canal, the axial transcutaneous pin including an external free end; and an external member configured to extend between the free ends of the pins and secure them relative to each other, and where the axial and radial pins are non-intersecting and are adapted to be coupled to one another subcutaneously through their mutual engagement with the bone only.

2. The fixation device of claim 1, wherein the axial transcutaneous pin includes a generally U-shaped transcutaneous section.

3. The fixation device of claim 1, further comprising a cover substantially enveloping the external member and external free ends of the pins.

4. The fixation device of claim 1, further including a second radial transcutaneous pin.

5. The fixation device of claim 1, wherein the bone is the radius and the fracture is located at the distal end of the radius.

6. The fixation device of claim 5, wherein the axial transcutaneous pin is configured to be installed through the distal end of the radius and extend proximally across the fracture.

7. The fixation device of claim 1, wherein the axial transcutaneous pin is configured to extend through the medullary canal across the fracture.

8. A fixation device use in repairing a fracture of a patient's bone, where the bone has a medullary canal, the device comprising:

a first intermedullary portion configured to extend longitudinally through a section of the medullary canal of the bone and span the fracture;

an external member configured to be disposed external to the patient;

a first transcutaneous portion configured to extend from the external member through the bone to the first intermedullary portion on a first side of the fracture; and a second transcutaneous portion configured to extend between and couple the external member and the bone on a second side of the fracture where the second transcutaneous portion and the first intermedullary portion are non-intersecting and the bone on the second side of the fracture can be manipulated relative to the bone on the first side of the fracture by moving the second transcutaneous portion relative to the first transcutaneous portion when the portions are engaged with the bone.

9. The fixation device of claim 8, wherein the first intermedullary portion takes the form of an intermedullary rod, and the first transcutaneous portion is a pin connected to the rod.

10. The fixation device of claim 8, further including a second intermedullary portion adapted to extend axially down the medullary canal, wherein the second transcutaneous portion is configured to extend fxom the external member through the bone to the second intermedullary portion and the first and second intermedullary portions are non-intersecting.

11. The fixation device of claim 8, wherein the second transcutaneous section includes a radial transcutaneous pin configured to be mounted in the bone generally radially to the medullary canal.

12. The fixation device of claim 8, wherein the external member is articulated to allow the positions of the transcutaneous sections to be adjusted relative to each other.

13. The fixation device of claim 8, wherein the transcutaneous sections, are clamped to the external member.

14. A fixation device for repairing a fracture of a bone having a medullary canal, the device comprising:

a radial transcutaneous pin configured to be mounted generally radially to the bone on a first side of the fracture, the radial transcutaneous pin including an external free end;

an axial transcutaneous pin configured to enter the bone on a second side of the fracture and extend axially down the medullary canal, the axial transcutaneous pin including an external free end, where the radial and axial pins are non-intersecting; and an external member configured to extend between the free ends of the pins and to secure them in an adjustable orientation relative to each other.

15. The fixation device of claim 14, wherein the external member is articulated to allow the free ends to be manipulated relative to each other to allow the bone on the first side of the fracture to be manipulated relative to the bone on the second side of the fracture.

16. The fixation device of claim 14, further including a second radial transcutaneous pin configured to be mounted generally radially to the bone on the first side of the fracture, the second radial transcutaneous pin including an external free to be secured by the external member.

* * * * *

UNITED STATES PATENT AND TRADEMARK OFFICE
CERTIFICATE OF CORRECTION

PATENT NO.  : 5,658,283
DATED       : August 19, 1997
INVENTOR(S) : Randall J. Huebner It is certified that error appears in the above-indentified patent and that said Letters Patent is hereby corrected as shown below:

In column 1, line 7, delete "8/636,326" and insert --8/636,266-- therefor.

In column 1, line 10, delete "5,545,1625" and insert --5,545,162-- therefor.

Signed and Sealed this

Twenty-seventh Day of January, 1998

Attest:

BRUCE LEHMAN

*Attesting Officer*    *Commissioner of Patents and Trademarks*